(12) United States Patent
Broens (10) Patent No.: US 9,724,036 B2
(45) Date of Patent: Aug. 8, 2017

(54) PROBE SYSTEM AND A PROBE FOR MEASURING FUNCTIONALITY OF AN ORIFICE IN THE HUMAN PELVIC REGION

(75) Inventor: Paulus Maria Antonius Broens, Groningen (NL)

(73) Assignee: Academisch Ziekenhuis Groningen, Groningen (NL)

( * ) Notice: Subject to any disclaimer, the term of this patent is extended or adjusted under 35 U.S.C. 154(b) by 699 days.

(21) Appl. No.: 13/509,608

(22) PCT Filed: Nov. 15, 2010

(86) PCT No.: PCT/NL2010/050758
§ 371 (c)(1),
(2), (4) Date: Jun. 28, 2012

(87) PCT Pub. No.: WO2011/059331
PCT Pub. Date: May 19, 2011

(65) Prior Publication Data
US 2012/0265044 A1    Oct. 18, 2012

Related U.S. Application Data

(60) Provisional application No. 61/267,466, filed on Dec. 8, 2009.

(30) Foreign Application Priority Data

Nov. 13, 2009   (EP) ..................................... 09175934

(51) Int. Cl.
*A61B 5/103*   (2006.01)
*A61N 1/05*    (2006.01)
(Continued)

(52) U.S. Cl.
CPC ............ *A61B 5/42* (2013.01); *A61B 5/04882* (2013.01); *A61B 5/227* (2013.01);
(Continued)

(58) Field of Classification Search
CPC . A61N 1/36007; A61N 1/0524; A61N 1/0512
(Continued)

(56) References Cited

U.S. PATENT DOCUMENTS 3,933,147 A    1/1976  Du Vall et al.
4,607,639 A *  8/1986  Tanagho et al. ................ 607/40
(Continued)

FOREIGN PATENT DOCUMENTS

BE   873368     5/1979
DE   19945600   3/2001
(Continued)

OTHER PUBLICATIONS

Sand, Peter K. et al. "Pelvic floor electrical stimulation in the treatment of genuine stress incontinence: A multi-center placebo-controlled trial." Am J Obstet Gynecol. vol. 173 No. 1. pp. 72-79.*
(Continued)

*Primary Examiner* — Adam J Eiseman
*Assistant Examiner* — Patrick Fernandes
(74) *Attorney, Agent, or Firm* — Patterson Intellectual Property Law, PC; Emily A. Shouse; Grant M. Ford (57) ABSTRACT

For measuring functionality of an orifice (16, 20) in the human pelvic region an elongated probe (4; 54) for insertion in the orifice (16, 20) is provided. The probe (4; 54) comprises one or more electrodes (5a-6a, 5b-6b, 6a-7a, 6b-7b; 55a-56a, 55b-56b, 56a-57a, 56b-57b, 57a-92a, 57b-92b) for stimulating receptors (23, 25) in tissue bounding the orifice (16, 20) and one or more muscle activity sensors (8a, 8b, 8c, 9a, 9b, 9c, 10a, 10b, 10c, 10d, 11a, 11b, 11e, 12a, 12b, 12c; 58a, 58b, 58c, 59a, 59b, 59c, 60a, 60b, 60c, 60d, 61a, 61b, 61c, 62) for sensing muscle activity causing pressure to be exerted by tissue bounding the orifice (16, 20). A control system (I) connected to the probe (4; 54) is arranged for outputting a neurostimulation signal (35) to the
(Continued)

electrode or electrodes and for registering a pressure signal or signals from the pressure sensor or sensors during a time interval directly subsequent to the outputting of the neurostimulation signal.

18 Claims, 5 Drawing Sheets

(51) Int. Cl.
    *A61B 5/00*          (2006.01)
    *A61B 5/0488*       (2006.01)
    *A61B 5/22*          (2006.01)
    *A61B 18/14*        (2006.01)
    *A61N 1/36*         (2006.01)
    *A61B 18/00*        (2006.01)
    *A61B 90/00*        (2016.01)

(52) U.S. Cl.
    CPC ........ *A61B 18/1492* (2013.01); *A61N 1/0512* (2013.01); *A61N 1/36007* (2013.01); *A61B 2018/00214* (2013.01); *A61B 2018/00898* (2013.01); *A61B 2090/064* (2016.02); *A61B 2562/0247* (2013.01)

(58) Field of Classification Search
    USPC .................................. 600/554, 587, 591, 593
    See application file for complete search history.

(56) References Cited

U.S. PATENT DOCUMENTS

| | | | |
|---|---|---|---|
| 4,873,990 A | | 10/1989 | Holmes et al. |
| 4,909,263 A | * | 3/1990 | Norris ............................. 607/39 |
| 5,924,984 A | | 7/1999 | Rao |
| 6,086,549 A | * | 7/2000 | Neese .................. A61N 1/0524 |
| | | | 600/554 |
| 6,185,465 B1 | | 2/2001 | Mo et al. |
| 6,741,895 B1 | * | 5/2004 | Gafni .................. A61B 5/4337 |
| | | | 600/38 |
| 7,079,882 B1 | * | 7/2006 | Schmidt ............... A61B 5/4041 |
| | | | 600/373 |
| 2003/0004434 A1 | | 1/2003 | Greco et al. |
| 2004/0054392 A1 | | 3/2004 | Dijkman |
| 2005/0283204 A1 | | 12/2005 | Buhlmann et al. |
| 2007/0265675 A1 | | 11/2007 | Lund et al. |
| 2009/0048639 A1 | * | 2/2009 | Chen .................. A61N 1/36007 |
| | | | 607/40 |
| 2009/0076565 A1 | * | 3/2009 | Surwit ........................... 607/41 |
| 2009/0222058 A1 | * | 9/2009 | Craggs ................. A61N 1/0512 |
| | | | 607/41 |

FOREIGN PATENT DOCUMENTS

| | | | | |
|---|---|---|---|---|
| DE | WO 2005096926 A1 | * | 10/2005 | ......... A61B 5/04882 |
| EP | 0366163 | | 5/1990 | |
| FR | 2767481 | | 2/1999 | |
| FR | 2774579 | | 8/1999 | |
| WO | 0234328 | | 5/2002 | |
| WO | 2005096926 | | 10/2005 | |
| WO | WO 2005096926 A1 | * | 10/2005 | |
| WO | 2006059338 | | 6/2006 | |
| WO | 2007055726 | | 5/2007 | |
| WO | 2007136266 | | 11/2007 | |
| WO | 2007145913 | | 12/2007 | |
| WO | 2008004234 | | 1/2008 | |

OTHER PUBLICATIONS

Siproudhis, Laurent et al, Fecal Incontinence With Normal Anal Canal Pressures: Where is the Pitfall?, The American Journal of Gastroenterology, vol. 94, No. 6, 1999, Elsevier Science, Inc.

Broens, Paul, Anorectal Sensibility, 2003, Thesis, Katholieke Universiteit Leuven, Belgie, 126 pages.

International Search Report for PCT/NL2010/050758 mailed Jun. 15, 2011.

Jaakko Malmivuo et al., Bioelectromagnetism—Principles and Applications of Bioelectric and Biomagnetic Fields, Chapter 21, 1995, Oxford University Press, New York, 15 pages.

* cited by examiner

PROBE SYSTEM AND A PROBE FOR MEASURING FUNCTIONALITY OF AN ORIFICE IN THE HUMAN PELVIC REGION

This application is a national phase entry under 35 U.S.C. §371 of PCT/NL2010/050758, filed Nov. 15, 2010, which claims priority and benefit of European Patent Application EP 09175934.0, filed Nov. 13, 2009, and from U.S. Provisional Patent Application No. 61/267,466, filed Dec. 8, 2009, each of which are hereby incorporated by reference in their entirety.

FIELD AND BACKGROUND OF THE INVENTION

The invention relates to a probe system and probe for measuring a function of an orifice in the human pelvic region.

Fecal and urinary incontinence are widespread problems entailing substantial embarrassment, discomfort and distress. Current treatments are surgery, physical exercises and drug therapy. However, in spite of significant research efforts, the success rates of such treatments has thus far been quite low, in particular where incontinence coincides with apparently adequate anal canal pressure and rectal filling sensations (see *Fecal Incontinence with Normal Anal Canal Pressures: Where is the Pitfall*; Laurent Shripoudhis et al.; Am J Gastroenterol 94: 1556-1563; 1999).

Disorders of control functions in the human pelvic region, such as urinal or anal dysfunction causing incontinence or constipation are commonly attributed to muscular disorders, causing insufficient muscle strength or stamina. In order to train these muscles and thereby improving the muscular fitness of the pelvic region of a patient, various probes have been developed that provide functional electric stimulation of muscles in the pelvic floor region. Such probes are to be inserted intravaginally or intraanorectally for stimulation of muscles in the region of the opening of which a dysfunction has been diagnosed.

EP 0 366 163 discloses a probe to be used intravaginally or intrarectally for taking recordings of pressure and of electromyography (EMG) during electrical stimulation for the principal purpose of properly fitting a patient with an electrical stimulator treatment device and also for diagnosing and monitoring of treatment. The probe is provided with either hydraulic or electrical pressure sensors for detecting the contraction of the pelvic floor muscles. The electrodes are each arranged adjacent to one of the pressure sensors to stimulate the pelvic floor muscles. Calibration marks on the proximal end of the vehicle assist the physician in the determination of the depth of vehicle insertion which provides the greatest contractile force of the muscles.

However, also sensation plays a role in pelvic orifice functionality. E.g. with respect to the fecal tract one can distinguish between rectal filling sensation and anal sampling sensation. Anal sampling sensations allow discrimination between gas, liquid and solid stool. In *Anorectal sensibility*; P. M. A. Broens; Dissertation; KU Leuven; Belgium 2003, sampling has been shown to be related to internal sphincter relaxation with pressure reduction in the proximal anal canal in response to rectal filling or contraction. Rectal filling was simulated by incremental distension of a rectal balloon while recording the volumes and pressures that trigger different levels of sensation. Filling sensations as reported by patients in response to neurostimulation were tested, but found not to correlate with filling sensations reported in response to the rectal filling volume or pressure parameters. It is suggested that a particular type of receptor is involved in sensing the level of filling sensation. Furthermore, the possible presence of distinct receptors for defecation was mentioned, but not found measurable by the electrosensitivity test.

SUMMARY OF THE INVENTION

It is an object of the present invention to provide a solution for measuring relevant indicators of the functionality of an orifice in the human pelvic region.

According to the invention, this object is achieved by providing a probe system for measuring functionality of an orifice in the human pelvic region, including:
an elongated probe for insertion in the orifice, the probe including:
  at least one electrode for stimulating receptors in tissue bounding the orifice, and
  at least one muscle activity sensor for sensing muscle activity causing pressure to be exerted by tissue bounding the orifice; and
a control system connected to the probe, the control system being arranged for:
  outputting a neurostimulation signal to the at least one electrode; and
  registering a muscle activity signal or signals from the at least one muscle activity sensor during a time interval directly subsequent to the outputting of the neurostimulation signal.

The invention can also be embodied in a probe for measuring functionality of an orifice in the human pelvic region, the probe being dimensioned for insertion in the orifice and including:
  at least one electrode for stimulating receptors in tissue bounding the orifice, and
  at least one muscle activity sensor for sensing muscle activity causing pressure to be exerted by tissue bounding the orifice;
wherein the muscle activity sensor or at least one of the muscle activity sensors is arranged for sensing muscle activity in a location spaced at least 0.5 cm in longitudinal direction of the probe from the electrode or at least one of the electrodes; and
wherein the muscle activity sensor or the at least one of the muscle activity sensors and the electrode or the at least one of the electrodes are connected for selectively receiving a stimulation signal by the electrode or the at least one of the electrodes and outputting a muscle activity signal by the muscle activity sensor or the at least one of the muscle activity sensors.

Furthermore, the invention can be embodied in a method for measuring functionality of an orifice in the human pelvic region, including:
inserting an elongated probe into the orifice, the probe including:
  at least one electrode for stimulating receptors in tissue bounding the orifice, and
  at least one muscle activity sensor for sensing muscle activity causing pressure to be exerted by tissue bounding the orifice; and
using a control system connected to the probe for:
  outputting a neurostimulation signal to the at least one electrode; and
  registering a muscle activity signal from the at least one muscle activity sensor during a time interval directly subsequent to the outputting of the neurostimulation signal.

By subjecting tissue containing receptors in a human pelvic region orifice to neurostimulation signals and measuring and registering how pressure exerted by tissue in the human orifice is affected by the stimulation of the receptors at least during a time interval directly subsequent to the stimulation, various aspects of the stimulus response relationship involving the neural receptors, pathways and interfaces as expressed in reflexes in response to the stimulation of the receptors (or the absence of such reflexes) can be registered. Measured characteristics of the reflexes can then be used as indicators for making a diagnosis of the cause of the perceived dysfunctionality of the orifice. In the present context, neurostimulation signals are understood to constitute stimulation signals that are to be sensed locally via submucosal receptors nearest to the electrode via which the neurostimulation signals is applied. Such neurostimulation signals are distinguished from direct muscle stimulation signals in that neurostimulation signals are too weak and/or too small to directly cause muscle activity as would be caused by applying muscle stimulation signals directly to a muscle or muscles.

Particular embodiments of the invention are set forth in the dependent claims.

Further objects, features, effects and details of the invention are described in the detailed description set forth below.

DETAILED DESCRIPTION

In FIGS. 1-4, an example of a probe system composed of a control system 1, signal transfer lines 2, 3 and a probe 4 is shown. The probe 4 according to the present example has a cylindrically shaped shank 44 with a diameter of 0.5 cm. Preferably, the diameter of the shank is between 0.25 and 2 cm. A stop 15 projects radially from the shank 44 at a distance of 5 cm from a distal end 13 of the probe 4 and constitutes an abutment for reliably maintaining the probe 4 inserted to a constant, maximum insertion depth. To ensure sufficient penetration depth for measuring in the relevant sections of the anal canal, the distance from the stop to the distal end of the probe is preferably at least 3.5 cm and more preferably at least 4 cm.

Figure 1:
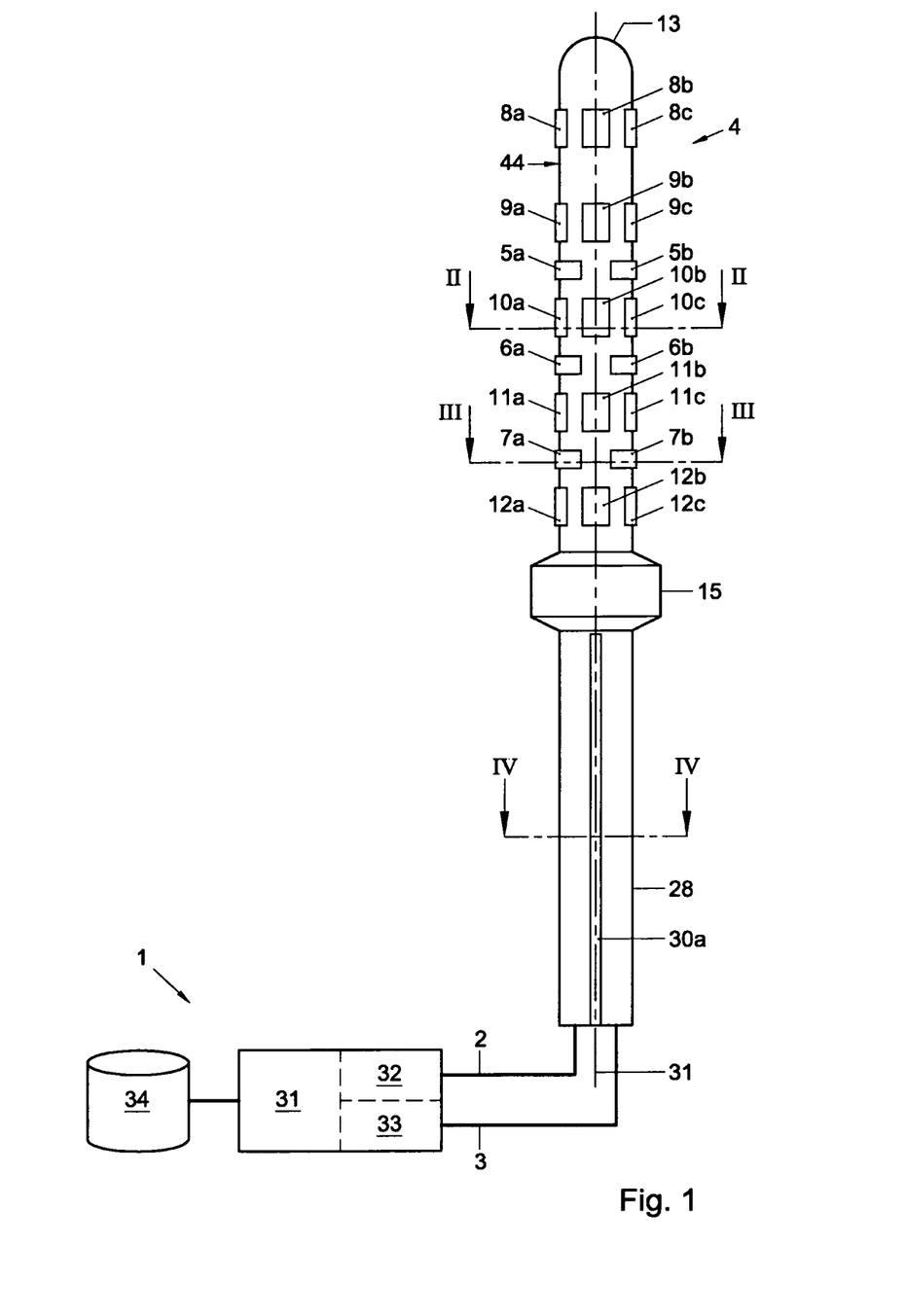
FIG. 1 is a schematic representation of an example of a probe system according to the invention including a probe according to the invention, with the probe shown in side view.
Figure 2:
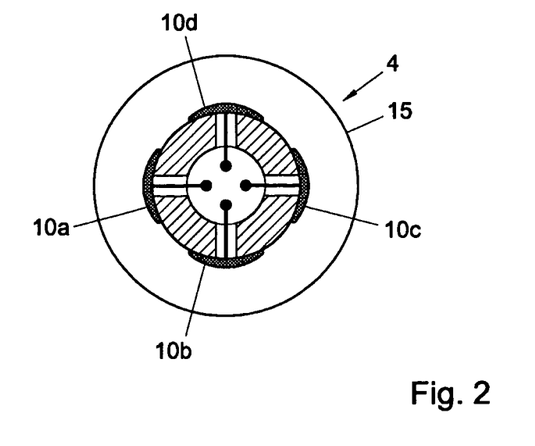
FIG. 2 is a cross-sectional view along the line II-II in FIG. 1.
Figure 3:
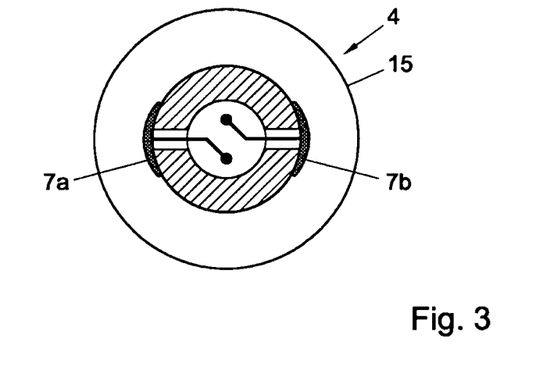
FIG. 3 is a cross-sectional view along the line in FIG. 1.
Figure 4:
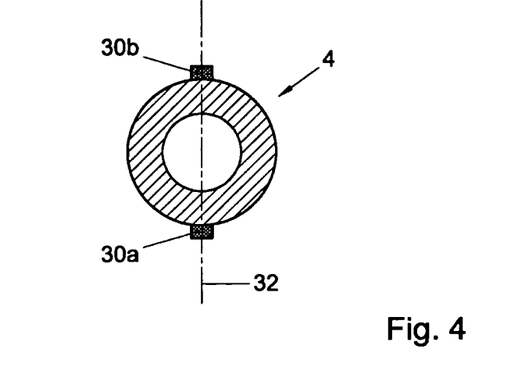
FIG. 4 is a cross-sectional view along the line IV-IV in FIG. 1.

It is observed that, where the terms "proximal" and "distal" refer to the position of portions of the probe, the terms "distal" and "proximal" are used in relation to the probe. The end 13 intended to be leading during insertion and oriented away from a handgrip 28 constitutes a distal end of the probe. Where the terms "proximal" and "distal" refer to the position of portions of the orifice and surrounding tissue, the terms "distal" and "proximal" are used as meaning away from the center to the outside of the torso and, respectively, to the inside of the torso.

The probe 4 further carries electrode contacts 5a, 5b, 6a-6b, 7a, 7b for contacting tissue to be stimulated. The contacts 5a, 5b, 6a-6b, 7a, 7b are arranged in two rows at laterally opposite sides of the shank 44 of the probe 4. The control system 1 is arranged for selectively outputting neurostimulation signals 35 via individual ones or sub-groups of the electrodes on one of said lateral sides of the probe only or simultaneously via electrodes on opposite lateral sides of the probe.

The electrodes shown are of a bipolar type in which each electrode is constituted by a pair of electrode contacts 5a-6a, 5b-6b, 6a-7a and 6b-7b. Thus, in the present example, adjacent bipolar electrodes 5a-6a and 6a-7a as well as adjacent bipolar electrodes 5b-6b and 6b-7b share common electrode contacts 6a and 6b. The electrodes may also be of a monopolar type, each electrode being constituted by a single electrode contact, although such electrode contacts generally provide less accurate control over the location where the stimulation signal is effectively applied. It is also conceivable to provide that more than two or up to all electrodes share a common electrode contact, for instance a contact extending in longitudinal direction along the non-shared electrode contacts.

The probe 4 further comprises muscle activity sensors 8a, 8b, 8c, 9a, 9b, 9c, 10a, 10b, 10c, 10d, 11a, 11b, 11c, 12a, 12b, 12c (not all muscle activity sensors are visible in FIGS. 1-4) arranged in four axial rows which are circumferentially distributed around the shank 44.

In the present examples, the muscle activity sensors are pressure sensors for sensing pressure exerted thereto by tissue bounding the orifice being examined. It however also possible to provide other types of muscle activity sensors, such as electrodes connected to circuitry for measuring an EMG as a measure of muscle activity, and more specifically muscle contraction, in the vicinity of the sensor. The electrodes for sensing muscle activity may be separate electrodes coupled to sensing circuitry only or electrodes that can coupled to both sensing and signal output circuitry, for instance via a switch.

For most purposes, a smaller number of rows, for instance a single row of pressure sensors that may be ring shaped or two rows of pressure sensors, preferably on laterally opposite sides of the shank portion may also be provided. Conversely, for obtaining an image of pressure distribution both in longitudinal sense and in circumferential sense with a higher resolution, a larger number of pressure sensors can be provided. In the present example, the pressure sensors each constitute a transducer generating electrical signals in response to pressure exerted thereon. However, the pressure sensors may also be of a different design, for instance in the form of sensors constituted by membranes or otherwise displaceable walls bounding a chamber containing a liquid, the interior of the chamber communicating with a transducer bounding the chamber or communicating therewith via a conduit.

The control system 1 includes a data processing unit 31, a signal generator 32 and a signal processing circuitry 33. The signal generator 32 is connected to the data processing unit 31 and, via signal feeding lines 2, to the electrodes 5a-6a, 6a-7a, 5b-6b and 6b-7b. The signal processing circuitry 33 is connected to the data processing unit 31 and, via signal pick-up lines 3, to the pressure sensors 8a, 8b, 8c, 9a, 9b, 9c, 10a, 10b, 10c, 10d, 11a, 11b, 11c, 12a, 12b, 12c. A memory 34 is connected to the data processing unit 31 for storing data representing stimulation signals or at least the time of output thereof and for storing measured pressures over time, preferably at least during a period of 30 seconds and more preferably 1 minute directly subsequent to the application of each stimulation signal. The signals representing measured pressure may be obtained by periodic sampling or as a continuous reading of a signal. The signal generator 32 may include a digital/analog converter for converting digital instructions into analog neurostimulation signals and the signal processing circuitry 33 may include an analog digital converter for converting analog signals from the pressure sensors into digital code representing the measured pressures. In the present example, the signal generator 31 and the signal processing circuitry 32 are arranged in the same housing as the data processing unit 31 and connected to the probe via a cable. It is, however, also conceivable, that transmitters and receivers are provided for wireless communication between, on the one hand, the probe 4 and, on the other hand, between the signal generator 31 and the signal processing circuitry 32. It is also conceivable to arrange the signal generator and the signal processing circuitry separate from the data processing unit, for instance in a housing of the probe. Communication between, on the one hand, the data processing unit and, on the other hand, the signal generator and the signal processing circuitry may then be in digital form either wired or wireless, for instance via a local area wireless connection protocol such provided for in the Bluetooth or Wifi (IEEE 802.11) standard.

In the present example, separate wires are each connected to one electrode contact 5a, 5b, 7a, and 7b while the central electrode contacts 6a, 6b are connected to the same conductor, so that each electrode 5a-6a, 5b-6b, 6a-7a and 6b-7b can be controlled separately to apply a stimulation signal exclusively via that electrode. Similarly, each pressure sensor 8a, 8b, 8c, 9a, 9b, 9c, 10a, 10b, 10c, 10d, 11a, 11b, 11c, 12a, 12b, 12c is connected to the signal processing circuitry 32 for separately receiving pressure signals from each of the pressure sensors. The (preferably electrical or optical) pressure signals represent the pressure or pressures sensed by the respective individual pressure sensor from which the pressure signal has been derived. Instead of separate connections to the electrodes and the pressure sensors, the pressure sensors may also be connected to a common signal bus system for multiplexed signal transfer.

The registration of the outputted neurostimulation signal may be constituted by the registration of the time of output, for instance by registration of the signal over time or just registration of a point or interval in time when outputting of the signal was started, reached its maximum, was ended or any point in-between. It is, however, also possible to provide that the neurostimulation signals are outputted in a predetermined sequence with a predetermined timing, for instance relative to a starting time. In that event the neurostimulation signals and the timing thereof is predetermined, at least relative to the starting time, and does not need to be registered each time the functionality of an orifice is measured. It is observed that, at least in absence of particular delay circuitry, for the purpose of the present measurements, the point in time of output of a neurostimulation signal by the control system 1 can effectively be considered as being the same point in time as the point in time at which the signal is applied at the location of the electrode.

The data processing unit 31 of the control system 1 is arranged for separately registering the signals received from each of the pressure sensors 8a, 8b, 8c, 9a, 9b, 9c, 10a, 10b, 10c, 10d, 11a, 11b, 11c, 12a, 12b, 12c over time and for associating each pressure signal or group of pressure signals to a stimulation signal directly preceding the time interval during which the measured pressure signal was picked-up. Preferably, the data processing unit is further arranged for determining a time delay between each outputted neurostimulation signal and the associated response signal received in response to the respective neurostimulation signal, as well as the peak level, average level and the duration of a pressure pulse represented by the pressure signal.

A proximal handgrip portion 28 of the probe 4 proximally of the stop 15 is provided with markings 30a, 30b which indicate a plane of symmetry 32 of the probe 4 parallel to its longitudinal axis 31. The plane of symmetry 32 should preferably be oriented parallel to the sagittal plane of the patient.

Figure 5:
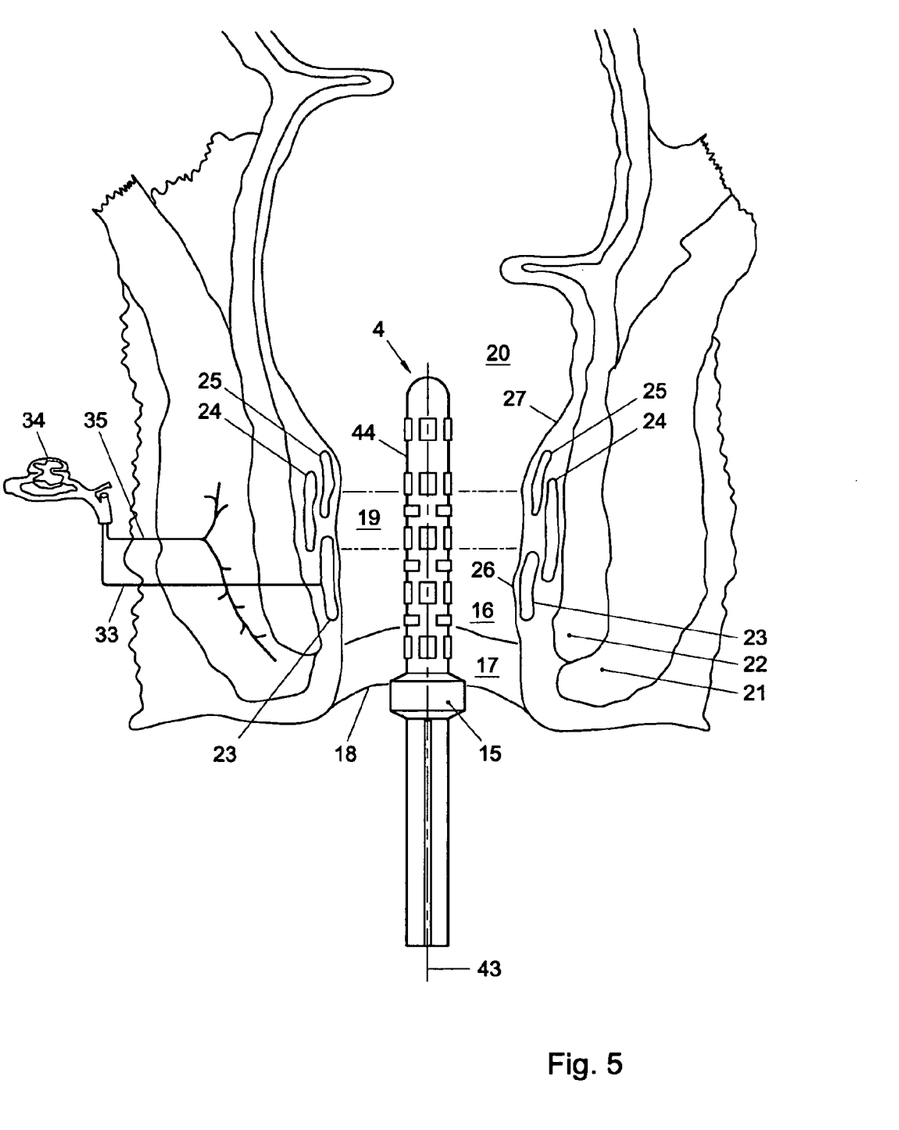
FIG. 5 is a schematic cross sectional view along the coronal plane of a central portion of a human pelvic region with a probe of the example shown in FIG. 1 inserted therein.

In FIG. 5, a central portion of a human pelvic region through which a rectum 20 and an anal canal 16 contiguous thereto extend is shown with the probe 4 of FIGS. 1-4 inserted in the anal canal 16 and in a lower portion of the rectum 20. In the anal canal 16, a distal anal canal portion 17, an anal verge 18 and a proximal anal canal portion 19 can be distinguished. The anal canal 16 is bounded by an anal wall 26 and the rectum 20 is bounded by a rectal wall 27, both in the form of epithelium and submucosal tissue. For illustrative purposes, the anal wall 26 is shown clear from the shank 44, but in practice the anal wall 26 will be in contact with the shank 44. Muscles surrounding the anal canal 16, the rectum 20 and the walls 26, 27 thereof include the external sphincter 21 and the internal sphincter 22. Fecal continence receptors 23, fecal filling sensation receptors 24 and defecation receptors 25 are located along the anal canal 16. Although it is common to use the word "receptor" in connection with cellular activities, in the present context, the word "receptor" is used to indicate submucosal corpuscles which are able to sense described changes in the anal canal. From the rectum 20 downward, the anatomy of the muscles, nerves and receptors is essentially bilaterally symmetrical and thus mirror symmetrical about the central sagittal plane. The defecation receptors 25 lie beneath the epithelium of the proximal anal canal 19 and provide positive feedback (a defecation reflex) causing rectal wall contraction via nerves constituting an intramural reflex pathway 36 (see FIG. 6). The continence type receptors 23 lie just beneath the anal epithelium at 0.5 to 3 cm above the anal verge 18. These receptors 23 are stimulated when stool enters the anal canal 16 and reinforce a fecal continence reflex in the form of involuntary contraction of the (apparently external) sphincter 21 via nerves 33 extending to the spinal cord 34 and nerves 35 extending from the spinal cord 34, thereby providing a spinal reflex pathway 33, 34, 35. The filling sensation receptors 24 are located deeper in the submucosa than the other receptors. Stimulation of these receptors 24 elicits a filling sensation signal making the person in question aware of the need to defecate and elicits a fecal filling sensation reflex via the brain to the intestines. If the need to defecate occurs, but circumstances do not allow to defecate immediately, the pelvic floor musculature contracts, which allows to consciously restrain stool.

In response to stool passing from the rectum 20 to the proximal anal canal portion 19, the defecation receptors 25 are stimulated instigating further contraction of the rectal wall 27 and thereby an increase of the pressure in the rectum 20 (the defecation reflex). Consequently, the anal canal 16 becomes filled with stool and the filling sensation receptors 24 are stimulated. Subsequently, when stool reaches the distal anal canal the continence receptors 23 are stimulated and the pressure in the distal anal canal 17 increases due to contractions of the external anal sphincter 21 and/or internal anal sphincter 22 preventing the descended stool from being ejected (the continence reflex). Thus, when functioning adequately, upon arrival of stool via the rectum 20, reflexes bring the stool in a position ready for defecation and prevent the stool from leaving the body. When the individual has reached a location suitable for fecal relief, such as a toilet, the individual can voluntarily relax the external anal sphincter 21 and defecate the stool that was brought in a position ready for defecation.

Incontinence may for instance be caused by dysfunction of the receptors, the reflex pathway and/or the associated muscles. Constipation may also be caused by dysfunction, albeit generally of a different nature, of the receptors, the reflex pathway and/or the associated muscles. Such dysfunctions affect the relationship between neurostimulation signals and the response in the form of pressure exerted by muscle contraction in different manners.

Figure 7:
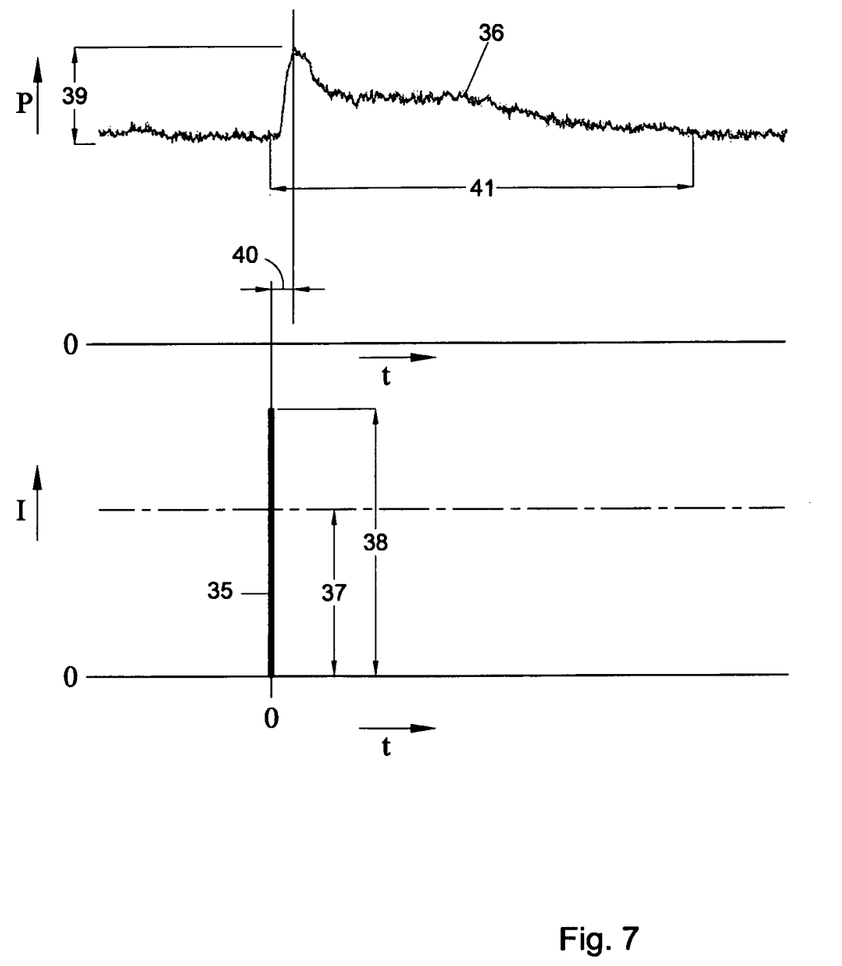
FIG. 7 is a diagram of an example of a measured relationship between a stimulus and a response signal over time.

In FIG. 7, as an illustrative example, a current-time (I-t) diagram 35 with time on the x-axis and a pressure-time (P-t) diagram 36 having the same time scale on the x-axis as the current time diagram 35 is shown. In the present example, the stimulation signal 35 is a representation of a current applied via the most distal electrodes 5a-6a, 5b-6b and the pressure signal represents the aggregated pressure as sensed by the pressure sensors at the level of sensors 11a-11c and at the level of the most proximal sensors 12a-12c, i.e. pressure indicative of the continence reflex.

If a receptor malfunctions, if a series of stimulation signals of varying magnitude 38 is applied, the threshold 37 above which the neurostimulation signal elicits a response in the form of a significant pressure increase 39 is either significantly higher or significantly lower than with individuals of which the receptors function normally, but the response delay time 40 has a regular value. If the spinal reflex pathway is hampered or lost, the threshold 37 above which a neurostimulation signal elicits a significant pressure increase 39 is a regular value, but the response delay time 40 is longer than normal or a significant pressure increase 39 is absent. When the reflex is absent, and the individual is continent by day, but only incontinent at night this might indicate that the individual only possesses of voluntary control over the relevant muscles. Muscle malfunction causes no substantial change of the threshold 37 above which a neurostimulation signal elicits a significant pressure increase 39 or of the delay 40, but the pressure increase 39 will generally be relatively small, of a brief duration 41, or level off relatively quickly. In severe cases, a response is absent. Thus, in total absence of a response, theoretically several options for the cause of the dysfunction are left open. However, since the defecation reflex and the continence reflex mechanisms can be distinguished, it will in many cases be possible to identify characteristics of reflexes for some of the mechanisms, which will allow narrowing down the possible cause of the dysfunction. In that light also the number of possible causes of a total absence of a response can in many cases be narrowed down. For instance, a general nerve disorder will mainly affect the continence reflex mechanism which involves signal transmission via the spinal reflex pathway 33, 34, 35.

In particular the continence receptors 23 and defecation receptors 25 can effectively be stimulated by electric neurostimulation pulses. The filling sensation receptors 24 are located deeper in the submucosal tissue and partially behind the continence receptors 23 and defecation receptors 25, so that electric neurostimulation of the filling sensation receptors 24 tends to be less direct and easily disturbed by co-stimulation of the continence receptors 23 and the defecation receptors 25. Nevertheless, a change in the angle between the anal canal caused by the contraction of the pelvic floor musculature resulting from a fecal filling sensation reflex causes a particular change in the pressure pattern, notably a relative increase of the pressure exerted on the axially central pressure sensors facing dorsally, which can be measured. A disturbance caused by co-stimulation of the continence receptors 23 and the defecation receptors 25 may be eliminated, at least to a large extent, by performing an additional measurement of the influence on the pressure pattern of stimulation or changes in stimulation of the continence receptors 23 and/or the defecation receptors 25 only (by applying the stimulation in axially spaced apart zones of the probe) and subtracting the influence on the pressure pattern of stimulation or changes in stimulation of the continence receptors 23 and/or the defecation receptors 25 only from the initially measured effect of the stimulation (in a zone located axially centrally relative to the spaced apart zones of the probe) of the filling sensation receptors 24.

To assess the functioning of the fecal continence reflex, the probe 4 is inserted in the anal canal 16 until the stop 15 is positioned against the anal verge 18. The anal wall 26 encloses the probe 4 and will be in contact with the electrodes 5a-6a, 5b-6b, 6a-7a and 6b-7b of which at least some are positioned opposite of the continence receptors 23 in the anal wall 26.

By selectively outputting neurostimulation signals to the electrodes 5a-6a, 5b-6b, 6a-7a and 6b-7b, selective electrical stimulation of the respective neural receptors nearest to the electrodes 5a-6a, 5b-6b, 6a-7a and 6b-7b can be achieved. The neurostimulation signals are weak enough to be sensed only locally via submucosal receptors opposite to or at least nearest to the electrode via which the neurostimulation signals is applied. The neurostimulation signals are too weak to cause a direct contraction response of the muscles involved in the reflexes to be measured or to be sensed by receptors spaced more than 0.5-1 cm from the electrode via which the stimulation signal is applied. To avoid that the stimulation signals constitute such direct muscle stimulation signals causing a direct contraction response, the stimulation signals are preferably smaller than a pulse width of 1 ms at an amperage of 15 mA and more preferably less than 10 mA and smaller than a pulse width of 0.1 ms at amperage of 30 mA or less and more preferably less than 20 mA.

The magnitude of the stimulation signals can be varied by varying the pulsewidth, for instance between 1 and 1000 μs and/or the amperage, for instance between 0.5 and 15 mA. The overall pulsewidth or pulse train duration and amperage may for instance be controlled by aggregating a plurality of modular pulses within a time interval amounting to the overall pulse width or pulse train duration. For effective neurostimulation while avoiding direct muscle stimulation, the overall pulsewidth or pulse train duration is preferably between 0.01 and 100 ms.

Furthermore, the position of the probe 4 determines the location where tissue will be stimulated. In advance, the precise location of the areas where the receptors 23, 24, 25 of the patient to be examined can be stimulated effectively are not known, as this is different not only between males and females but also between individuals. To determine which of the electrodes provide the most effective stimulation of the respective receptors 23, 25, neurostimulation signals, preferably of the same magnitude (in terms of pulse width and amperage or voltage), can selectively be outputted to first ones of the electrodes 5a-6a, 5b-6b and subsequently to next ones of the electrodes 6a-7a and 6b-7b in a different position in longitudinal direction of the probe than the first ones of the electrodes. The order in which the signals are outputted to the electrodes can for instance be from distal to proximal, from proximal to distal. If three, four or more electrodes are provided in different positions in longitudinal direction of the probe, the signals can be outputted via the electrodes in an order that leaves a relatively large distance between the electrodes to which successive signals are outputted. This may be advantageous to avoid artifacts due to changes in sensitivity of the receptors caused by a stimulation signal previously applied in close vicinity. The electrode or group of electrodes that elicit the strongest and/or most consistent responses in the area of the distal anal canal 17 (sensed by the pressure sensors 11a, 11b, 11c, 12a, 12b, 12c proximal of the electrodes 5a-6a, 5b-6b or the electrodes 6a-7a and 6b-7b via which the stimulation signals eliciting that response have been applied) can be assumed to be in best electrical contact with the continence receptors 23. Responses sensed at the pressure sensors 8a, 8b, 8c, 9a, 9b, 9c distally of the electrodes 5a-6a, 5b-6b or the electrodes 6a-7a and 6b-7b, via which the stimulation signals eliciting that response have been applied, indicate the defecation receptors 25 have been stimulated. In the example shown in FIG. 2 such responses are unlikely to occur, but for a patient having defecation receptors 25 closer to the anal verge 18, such responses do occur.

The continence receptors 23 are generally located in an area from 0.2 cm to 3 cm above the anal verge 18. To ensure that these receptors 23 can be stimulated, the probe preferably has electrodes in axially different locations in a zone between 0.2 cm and 3 cm from the stop 15. Since the zone where the continence receptor 23 can be stimulated is typically located inwardly of the zone of the anal canal 16 where sphincter contraction generates most pressure, the probe preferably has pressure sensors located proximally of all of the electrodes and also pressure sensors proximally neighboring each of the electrodes. Thus pressure generated can be detected reliably irrespective whether the area where the sphincter contraction pressure occurs is located close to or more remote from the area where the continence receptors 23 can be stimulated effectively.

Next the measurement of the reflexes is carried out. For measuring the continence reflex, the control system 1 outputs neurostimulation signals of varying magnitude, preferably to the electrodes via which, during the previous, successive, selective application of neurostimulation signals via different electrodes, the strongest or most consistent response at the proximal pressure sensors 11a, 11b, 11c, 12a, 12b, 12c have been elicited. The stimulation signal is for instance supplied to the electrodes 5a-6a, 5b-6b or to the more proximal electrodes 6a-7a, 6b-7b. Then, the signals received from the pressure sensors 11a, 11b, 11c, 12a, 12b, 12c indicative of contraction of the sphincters, 21, 22 are registered and associated to the respective stimulation signals.

Generally, the pressure response of the fecal continence reflex can be sensed particularly effectively by pressure sensors spaced at least 0.5 cm and in most cases at least 1 cm proximally from the electrode via which the associated neurostimulation signal has been applied. A continence reflex or its disturbance may also affect pressure sensed by sensors spaced at least 0.5 cm and in most cases at least 1 cm distally from the electrode via which the associated neurostimulation signal has been applied. Measurements of such contribution can be advantageous for better distinguishing and/or characterizing a pressure pattern over the length of the probe caused by a continence reflex. Comparing such patterns with reference patterns can be helpful to identify dysfunctionality types.

The response signal 36 shown in FIG. 7 may represent the pressure as sensed by, a single pressure sensor, the average pressure sensed by a group of pressure sensors, such as a group of pressure sensors in the same position or zone in longitudinal direction of the probe 4. Apart from the maximum change in pressure 39, it is also possible to register an average pressure increase over for instance a second or half a second from the moment of stimulation or a rate of pressure reduction subsequent to the maximum pressure.

If the stimulation of the continence receptors 23 has resulted in the receptors 23 transmitting signals via the corresponding spinal reflex pathways causing the muscles of the external and/or internal sphincter 21, 22 to contract the passage of the signals through this pathway causes the response signal to be delayed in time with respect to the trigger signal as is illustrated in FIG. 7 by a delay 40. The data processing unit 31 of the control system 1 is programmed so that it automatically determines and registers the delay 40 between the stimulation signal and the response signal or signals from the pressure sensor or sensors. The generation and outputting of stimulation signals and the registration of response signals and the determination of the time delay is then repeated to allow threshold levels, magnitudes and delays of response signals to be determined from the measurement results. In some cases or for some receptors no response may be obtained. Such occurrences are also registered in the non-transitory memory 34.

By separately stimulating one or more electrodes 5a-6a, 6a-7a or 5b-6b, 6b-7b to the left or to the right of the sagittal plane 43 and measuring a difference between the reaction to the signals applied to the electrodes 5a-6a, 6a-7a or 5b-6b, 6b-7b to the left and, respectively, to the right of the sagittal plane 43, relative dysfunction of receptors and/or reflex pathways to the left or to the right of the sagittal plan can be measured.

Figure 6:
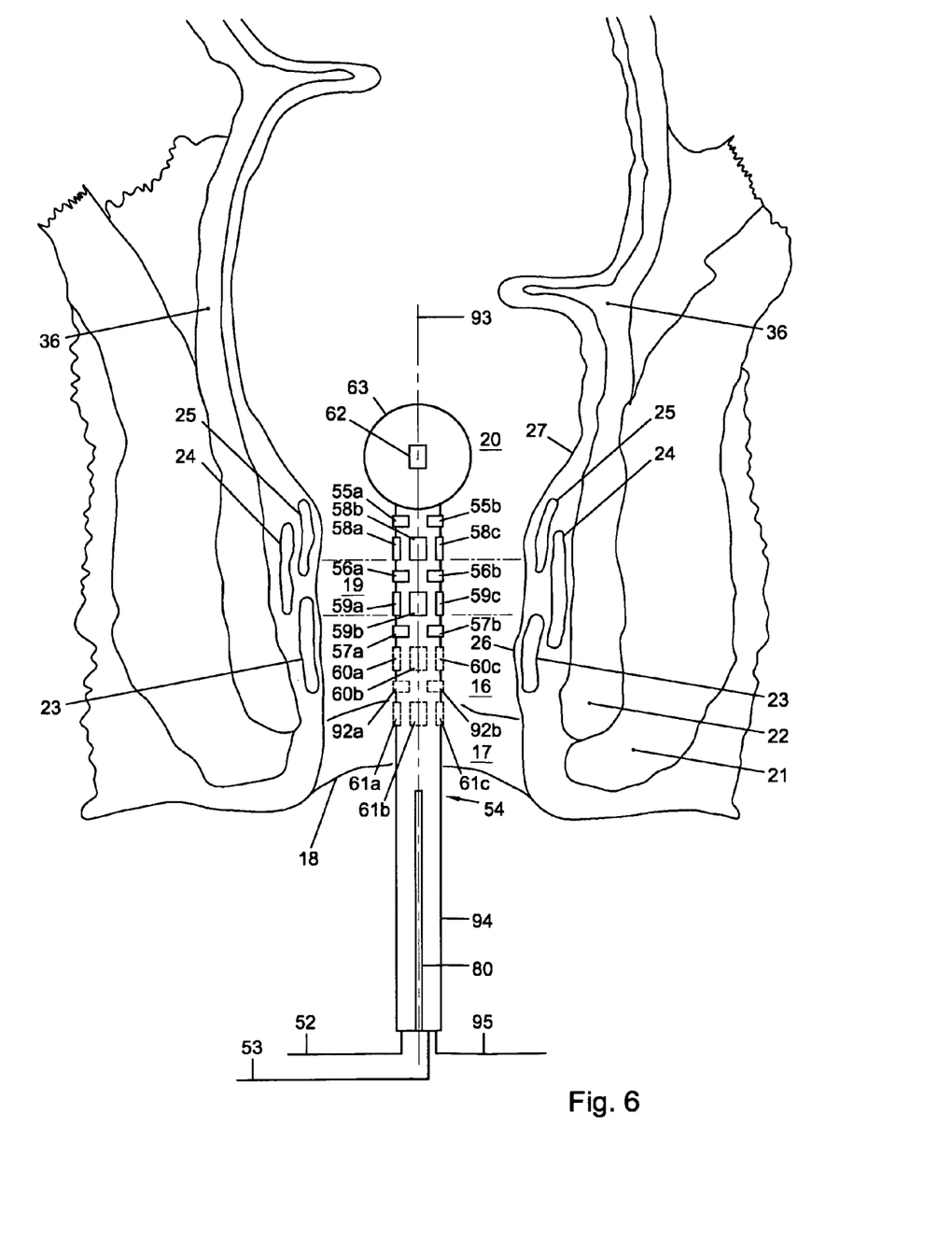
FIG. 6 is a schematic cross sectional view along the coronal plane of a central portion of a human pelvic region with another probe according to the invention.

In FIG. 6, a second example 54 of a probe according to the invention is shown. The probe 54 according to this example is specifically suitable for measuring defecation reflexes. The probe 54 has a distal end in the form of an inflatable balloon 63. For inflating the balloon 63 a conduit extends through a shank 94 of the probe 54 and via tubing 95 connectable to a pump for pumping a medium into the balloon 63 and for allowing the medium to be discharged from the balloon 63.

By inserting the probe 54 with the balloon 54 in non inflated condition until the balloon 63 is in the rectum 20, subsequently inflating the balloon 63 and then retracting the probe 54 until the balloon 63 rests against the lower end of the rectum 20, where the rectum 20 narrows towards the anal canal 17, it is reliably ensured that the portion of the probe 54 proximally adjacent of the balloon 63 is positioned in the upper (proximal) portion 19 of the anal canal 16. In this portion 19 of the anal canal 16, the defecation receptors 25 are located. Since the probe 54 is positioned relative to the transition of the rectum 20 to the anal canal 16, the probe according to this example is not equipped with an abutment projecting from the shank 94 of the probe 54. It is however conceivable to provide an abutment that is slidable along the shank and releasably fixable in longitudinal direction of the probe to maintain the probe in position after the probe has been retracted until the balloon has been seated against the lower end of the rectum.

Preferably, the balloon 63 has a cross-sectional size that is sufficient to contact the rectum wall 27 so that pressure in the balloon 54 increases when the rectum 20 contracts as part of a defecation reflex. For an accurate pressure transfer, the balloon 63 is preferably filled with a fluid, which may be a liquid or a gas or contain both. Furthermore, the balloon wall is preferably of a material that is stiff in longitudinal direction to avoid pressure relief caused by stretching of the balloon 63 in longitudinal direction. The balloon 63 can have a spherical shape as shown, but other shapes, such as pear shape, rugby ball shape or a cylindrical shape with rounded and/or conical ends are also possible. The balloon 63 is radially expandable from a configuration substantially within the shank 94 or within a continuation of a cross-sectional profile of the shank 94 to a configuration extending radially beyond the continuation of the cross-sectional profile of the shank 94. The shank may have a portion distally of the balloon. In such an embodiment, the expanded balloon extends radially out of the shank.

The probe 54 has four electrodes 55a-56a, 55b-56b, 56a-57a and 56b-57b sharing central electrode contacts 56a, 56b arranged two by two on opposite sides of a central plane 93 of the probe 54 marked by markings 80 on diametrically opposite sides of the shank 94 of the probe 54. The electrodes are connected to signal transfer lines 52 for allowing signals to be applied selectively to each electrode (i.e. electrode contact pair) 55a-56a, 55b-56b, 56a-57a and 56b-57b. The electrodes for stimulating the defecation receptor 25 are preferably arranged to apply neurostimulation via the upper zone of the anal canal when the probe is inserted with the balloon 63 against the downstream end of the rectum. To achieve this, the electrodes are preferably at least partially arranged at less than 1.5 cm, and more preferably at less than 0.5 cm, from the proximal end of the balloon 63.

The probe has two groups of pressure sensors arranged in groups of four circumferentially distributed pressure sensors 58a, 58b, 58c and 59a, 59b, 59c on the outer surface of the shank 94 and a pressure sensor 62 for measuring the pressure in the balloon 63 which constitutes a measure for the pressure exerted by the rectal wall 27 onto the balloon 63. The pressure sensor 62 is shown in a position in the balloon 63, but may also be arranged in a position outside the balloon 63 but communicating with the internal space of the balloon 63 or in positions on the outside of the balloon or of another expandable member. The pressure sensors 58a, 58b, 58c, 59a, 59b, 59c, 62 are connected to pressure signal transfer lines 53 for allowing distinct pressure signals to be supplied to the processing circuitry 33 from each of the pressure sensors 58a, 58b, 58c, 59a, 59b, 59c, 62.

Prior to measurement and registration of defecation reflexes, neurostimulation signals are outputted selectively to the electrodes 55a-56a and 55b-56b and then to the other electrodes 56a-57a and 56b-57b in different positions in longitudinal direction of the probe 54. The electrodes, via which applied neurostimulation signals cause the strongest and/or most consistent pressure increases measured by the pressure sensor 62 measuring the pressure in the balloon 63, are successively used for outputting mutually different neurostimulation signals for measuring defecation reflexes. If, in response to the outputting of neurostimulation signals via the electrodes 55a-56a and 55b-56b or the electrodes 56a-57a and 56b-57b, pressure increases are signaled by the pressure sensors 58a, 58b, 58c, 59a, 59b, 59c, it is likely that this has resulted from stimulating the continence receptors 23 as well, in particular if the pressure increase is relatively large. To avoid disturbances of the measurement of the defecation reflex by continence reflexes, it is preferred not to apply neurostimulation signals via electrodes via which a continence reflex is triggered. By changing the axial position of the probe and/or selecting different electrodes via which the neurostimulation signal is applied until a pressure response of the internal sphincter (here sensed by the pressure sensors 58a, 58b, 58c, 59a, 59b, 59c) is absent or minimal, stimulation of the continence receptors 23 can be avoided.

For measurement and registration of defecation reflexes, the defecation receptors 25 are stimulated. To that end, the control system 1 outputs stimulation signals of various magnitudes to for instance the most distal electrodes 55a-56a, 55b-56b and/or to the most proximal electrodes 56a-57a, 56b-57b of the probe 54. Neurostimulation signals may also be outputted to one or more electrodes to the left or to the right of the sagittal plane 93 only, to measure differences between responses obtained by stimulation of the defecation receptors 25 to the left or, respectively, to the right of the sagittal plane 93 only.

In a time interval starting with each neurostimulation signal, signals received from the pressure sensor 62 in the balloon 63 are registered. Similarly to the measurement of the continence reflex, the response signal 36 (see FIG. 7) represents the measured pressure over time, a pressure increase 39 being elicited by the stimulation signal applied to the receptors 25. Since this reflex involves the passage of signals from the receptors to the musculature via the intramural reflex pathway 36, which does not pass via the spinal reflex pathway so overall pathway length is relatively short, any significant delay 40 between a neurostimulation signal and the response signal associated thereto will be relatively small. The procedure for determining the characteristics of the relationship between the stimulation signal and the response signal with respect to threshold value 37 of the stimulation signal, characteristics of the magnitude 39, 41 of the response signal and the temporal dependency (delay and duration) of the response is similar to the procedure for the measurement of the continence reflex.

While the invention has been illustrated and described in detail in the drawing and foregoing description, such illustration and description are to be considered illustrative or exemplary and not restrictive; the invention is not limited to the disclosed embodiments.

For instance, a probe suitable for measuring both the continence reflex and the defecation reflex may be obtained by providing a probe as shown in FIG. 6 with further electrodes 57a-92a, 57b-92b, and further, more proximal groups of pressure sensors pressure 60a, 60b, 60c, 61a, 61b, 61c. Preferably, the electrodes 57a-92a, 57b-92b are located at least 2.5 cm from the expandable member 63. During the determination which electrodes to use for measuring characteristics of the reflexes, the electrodes via which the best pressure responses via the sensor 62 are elicited can then be selected as the electrodes via which signals are applied for stimulating the defecation receptors 25. The electrodes via which the best pressure responses via the pressure sensors 60a, 60b, 60c, 61a, 61b, 61c more remote from the expandable member 63 are elicited can then be selected as the electrodes via which signals are applied for stimulating the continence receptors 23.

Furthermore, the number of columns in which electrodes are arranged in an axial direction located at the probe member can be expanded or reduced, to allow variation of the stimulation site in the angular direction with regard to the probe.

A probe system according to the invention with a suitably dimensioned probe can be used for measuring reflexes in these orifices as well.

For instance, for measurements in urethra, the neurostimulation signals may be applied to receptors along the urethra, at various locations in longitudinal direction of the urethra between the bladder and the internal and external sphincter and pressure responses in the bladder and in a section of the urethra surrounded by the internal and external sphincter may be measured (for men stimulation and/or sensing of pressure responses may also take place in a section of the urethra inside the prostate.

To this end, the probe is preferably equipped with an expandable member, such as a balloon, a structure with flexible, longitudinally oriented ribs that can be buckled to a relatively large width or an umbrella structure, stimulation electrodes in a zone of up to 2 to 3 cm proximally of the expandable structure and pressure sensors for sensing pressure in the bladder and in a zone proximally of the zone of 2 to 3 cm where the stimulation electrodes are located. Thus, the electrodes and the pressure sensors are connected to allow measurement of pressure changes in zones distally and proximally spaced from a zone where, during a given measurement, stimulation signals are applied exclusively.

Receptors of reflex pathways in the area of the vagina are located in the mons veneris, labia majora, clitoris, labia minora and the hymenal ring. These receptors are located distally (from the perspective of the patient) of the musculature that is stimulated to contract via a reflex pathway as a reflex in response to stimulation of the receptors. A probe for measurement of the functionality of reflexes of the vaginal area preferably has stimulation electrodes in a zone proximally of a zone in which the pressure sensors are located. The electrodes and the pressure sensors are connected to allow measurement of pressure changes in a zone distally spaced from the zone where, during a given measurement, stimulation signals are applied exclusively.

The cross-section of the shank does not have to be circular, but may also be of another shape, such as oval or clover leaf shaped.

Instead of by a stop, the distance over which the probe can be inserted, and accordingly the proximal end of the probe portion to be inserted may also be determined otherwise, for instance by a marking. The marking or the stop may be releasably fixed and displaceable in longitudinal direction of the probe when released to allow the probe to be accommodated to different individuals, in particular with respect to the location of the distal end. This is of particular relevance if the distal end portion includes an expandable member providing positioning of the probe in its longitudinal direction relative to the transition of the rectum to the anal canal.

Furthermore, the probe can be accommodated with various types of handles to allow easy maneuvering of the probe.

Other variations to the disclosed embodiments can be understood and effected by those skilled in the art in practicing the claimed invention, from a study of the drawings, the disclosure, and the appended claims.

What is claimed is:

1. A probe system for measuring functionality of an orifice in the human pelvic region, comprising:
    an elongated probe for insertion in the orifice, the probe comprising:
        at least one electrode for stimulating receptors in tissue bounding the orifice, and
        muscle activity sensors for sensing muscle activity causing pressure to be exerted by tissue bounding the orifice, the muscle activity sensors being spaced in longitudinal direction of the probe from the at least one electrode and including at least one sensor proximally spaced from the at least one electrode and at least one sensor distally spaced from the at least one electrode; and
    a control system connected to the probe, the control system being arranged for:
        outputting a neurostimulation signal to the at least one electrode, the neurostimulation signal configured for application to the tissue containing the receptors in the human pelvic region orifice, wherein the neurostimulation signal is of a magnitude for eliciting a muscle reflex via a reflex pathway and too weak and/or too small to cause the muscle activity by direct muscle stimulation;
        registering, during a time interval directly subsequent to the outputting of the neurostimulation signal, a first muscle activity signal or first muscle activity signals from at least one of the muscle activity sensors located proximally of the electrode or at least one of the electrodes stimulating the receptors and a second muscle activity signal or second muscle activity signals from at least one of the muscle activity sensors located distally of the electrode or at least one of the electrodes stimulating the receptors, the first muscle activity signal or signals being registered separately from the second muscle activity signal or signals; and
        determining a duration of a time delay between the outputted neurostimulation signal and a change in the muscle activity signal or signals received from at least one of the muscle activity sensors.

2. A probe system according to claim 1, comprising at least two of said electrodes distributed in longitudinal direction of the probe, wherein the control system is arranged for separately outputting said neurostimulation signal only via individual ones or subgroups of said electrodes.

3. A probe system according to claim 1, comprising at least two of said electrodes located diametrically opposite of each other on laterally opposite sides of the probe wherein the control system is arranged for selectively outputting said neurostimulation signal only via individual ones or subgroups of said electrodes on one of said laterally opposite sides of the probe or simultaneously via electrodes on both said laterally opposite sides of the probe.

4. A probe system according to claim 1, wherein at least two of the muscle activity sensors are located diametrically opposite of each other on laterally opposite sides of the probe and wherein the control system and the muscle activity sensors are connected for separately registering muscle activity signals from individual ones or groups of the muscle activity sensors on each of said laterally opposite sides of the probe.

5. A probe system according to claim 1, wherein the control system is arranged for generating the neurostimulation signal as an electric pulse or a plurality of electric pulses, each smaller than a signal having an amperage of 15 mA at a duration of 1 ms and a signal having an amperage of 30 mA at a duration of 0.1 ms.

6. A probe for measuring functionality of an orifice in the human pelvic region, the probe being dimensioned for insertion in the orifice and comprising:
    a shank;

at least one electrode for stimulating receptors in tissue bounding the orifice;

at least one muscle activity sensor for sensing muscle activity causing pressure to be exerted by tissue bounding the orifice;

a balloon distally of said at least one electrode, the balloon being radially expandable from a configuration within the shank or within a continuation of a cross-sectional profile of the shank to a configuration extending radially beyond the shank or beyond the continuation of a cross-sectional profile of the shank; and a control system connected to the probe, the control system arranged for:
  outputting a neurostimulation signal to the at least one electrode, the neurostimulation signal configured for application to the tissue containing the receptors in the human pelvic region orifice, wherein the neurostimulation signal is of a magnitude for eliciting a muscle reflex via a reflex pathway and too weak and/or too small to cause the muscle activity by direct muscle stimulation; and
  registering, during a time interval directly subsequent to the outputting of the neurostimulation signal, a first muscle activity signal or first muscle activity signals from at least one of the muscle activity sensors located proximally of the electrode or at least one of the electrodes stimulating the receptors and a second muscle activity signal or second muscle activity signals from at least one of the muscle activity sensors located distally of the electrode or at least one of the electrodes stimulating the receptors, the first muscle activity signal or signals being registered separately from the second muscle activity signal or signals; and
  determining a duration of a time delay between the outputted neurostimulation signal and a change in the muscle activity signal or signals received from at least one of the muscle activity sensors, wherein the at least one muscle activity sensor or at least one of the muscle activity sensors is arranged for sensing muscle activity in a location spaced distally in longitudinal direction of the probe from the electrode or at least one of the electrodes;

wherein said electrode or said at least one of the electrodes is connected for selectively receiving a stimulation signal by said electrode or said at least one of the electrodes;

wherein said at least one muscle activity sensor is connected for selectively outputting a muscle activity signal by said at least one muscle activity sensor; and wherein said at least one muscle activity sensor is a pressure sensor mounted in the balloon or communicating with an internal space of the balloon for sensing pressure exerted on the balloon by measuring pressure in the balloon.

7. A probe according to claim 6, wherein the shank carries at least one further muscle activity sensor in a position at least 2.5 cm from the balloon.

8. A probe according to claim 6, wherein the shank carries the at least one electrode in a position less than 1.5 cm from the balloon.

9. A probe according to claim 6, comprising at least one further electrode and transmission channels, wherein the transmission channels and one or a subgroup of the electrodes are connected for separate communication of each or each subgroup of said electrodes with the control system.

10. A probe according to claim 6, comprising at least one further muscle activity sensor and comprising transmission channels each connected to one of the muscle activity sensors for separately connecting each or each subgroup of said muscle activity sensors to a control system.

11. A probe according to claim 7, wherein the electrode is located in a zone between 0.2-3 cm from a proximal end of the probe portion to be inserted.

12. A probe according to claim 6, wherein the at least one muscle activity sensor is a pressure sensor for sensing pressure exerted by tissue bounding the orifice.

13. A method for measuring reflexes in the human anal canal or urethra, comprising:
  inserting an elongated probe into the anal canal or urethra, the probe comprising:
    at least one electrode stimulating receptors in tissue bounding the orifice, and
    muscle activity sensors sensing muscle activity causing pressure to be exerted by tissue bounding the orifice, the muscle activity sensors being spaced in longitudinal direction of the probe from the at least one electrode and including at least one sensor proximally spaced from the at least one electrode and at least one sensor distally spaced from the at least one electrode; and
  using a control system connected to the probe for:
    outputting a neurostimulation signal to the at least one electrode, the neurostimulation signal applied to the tissue containing the receptors in the human pelvic region orifice being too weak and/or too small to cause the muscle activity by direct muscle stimulation, the neurostimulation signal eliciting muscle activity via a reflex pathway; and
    registering, during a time interval directly subsequent to the outputting of the neurostimulation signal, a first muscle activity signal or first muscle activity signals from at least one of the muscle activity sensors located proximally of the electrode or at least one of the electrodes stimulating the receptors and a second muscle activity signal or second muscle activity signals from at least one of the muscle activity sensors located distally of the electrode or at least one of the electrodes stimulating the receptors, the first muscle activity signal or signals being registered separately from the second muscle activity signal or signals.

14. A probe system according to claim 1, wherein the at least one muscle activity sensor is a pressure sensor for sensing pressure exerted by tissue bounding the orifice.

15. A probe according to claim 1, having a shank carrying the at least one electrode, the shank having a diameter of 0.25-2 cm.

16. A method according to claim 13, wherein further comprising, determining for each of the first and second muscle signals, a duration of a time delay between the outputted neurostimulation signal and a change in the muscle activity signal or signals received from at least one of the muscle activity sensors.

17. A probe system according to claim 6, wherein the control system is configured to select said electrode or said at least one of the electrodes for selectively receiving the stimulation signal based at least in part upon a pressure change measured by the pressure sensor.

18. A probe system according to claim 6,
  wherein the probe further includes at least one further muscle activity sensor located proximally of said at least one electrode; and wherein the control system is configured to select said electrode or said at least one of the electrodes for selectively receiving the stimulation signal based at least in part upon a pressure change measured by the further muscle activity sensor located proximally of said at least one electrode being absent or minimal.

\* \* \* \* \*